United States Patent [19]

Niki et al.

[11] Patent Number: 4,619,754

[45] Date of Patent: Oct. 28, 1986

[54] CHEMICALLY MODIFIED ELECTRODES AND THEIR USES

[75] Inventors: Katsumi Niki; Katsuyoshi Kobayashi, both of Yokohama; Hiroo Inoguchi, Okazaki; Tatsuhiko Yagi, Shizuoka, all of Japan

[73] Assignee: Ajinomoto Company Incorporated, Tokyo, Japan

[21] Appl. No.: 473,207

[22] Filed: Mar. 8, 1983

[30] Foreign Application Priority Data

Mar. 9, 1982 [JP] Japan ................................. 57-36870

[51] Int. Cl.$^4$ ............................................. C25B 11/20
[52] U.S. Cl. ............................... 204/290 R; 204/403; 358/902; 435/817
[58] Field of Search ................... 204/192 C, 400, 403, 204/416, 418, 290 R, 290 F, 299; 358/902; 435/817, 291; 427/38, 41, 44

[56] References Cited

U.S. PATENT DOCUMENTS

| | | | |
|---|---|---|---|
| 3,510,418 | 5/1970 | Mizutani et al. | 204/296 |
| 3,758,396 | 9/1973 | Vieth et al. | 204/296 |
| 3,966,580 | 6/1976 | Janata et al. | 204/403 |
| 4,151,049 | 4/1979 | Janata | 204/418 |
| 4,224,125 | 9/1980 | Nakamura et al. | 204/403 |
| 4,297,173 | 10/1981 | Hikuma et al. | 435/817 |
| 4,350,763 | 9/1982 | Suzuki et al. | 435/817 |
| 4,464,235 | 8/1984 | Simon et al. | 435/173 |
| 4,490,464 | 12/1984 | Gorton et al. | 204/290 R |

OTHER PUBLICATIONS

Grot, Walther, "Use of Nafion Perfluorosulfonic Acid Products as Separators in Electrolytic Cells", *Chem.-Ing.-Tech.*, 50 (1978), Nr. 4, pp. 299–301.

Chemical Abstracts, vol. 97, No. 26, 27 Dec. 1982, p. 628, col. 1, Abstract No. 225404n.

Chemical Abstracts, vol. 73, No. 18, 2 Nov. 1970, p. 231, col. 1, Abstract No. 91133s.

Chemical Abstracts, vol. 97, No. 16, 18 Oct. 1982, p. 556, col. 1, Abstract No. 135589x.

Rubinstein et al, "Polymer Films on Electrodes", J. Am. Chem. Soc., 1981, 103, 5007–5013.

White et al, "Polymer Films on Electrodes", J. Am. Chem. Soci., 1982, 4811–4817.

Berezin et al, Chemical Abstracts, vol. 85, No. 22, 29 Nov. 1976, p. 196, col. 2, Abstract No. 163224v.

*Primary Examiner*—John F. Niebling
*Assistant Examiner*—Terryence Chapman
*Attorney, Agent, or Firm*—Oblon, Fisher, Spivak, McClelland & Maier

[57] ABSTRACT

An electrically conducting solid electrode having a surface on which a nitrogen-containing electron mediator and a strong acidic cation exchange resin containing aromatic groups are immobilized is disclosed along with methods for producing this electrode and uses therefor.

10 Claims, No Drawings

CHEMICALLY MODIFIED ELECTRODES AND THEIR USES

The invention relates to the preparation of surface chemically modified electrically conducting solid electrodes and their uses.

It has been well known that electrically conducting solid electrode surfaces can be modified by redox polymers. However, the activity of this modified electrode varies with the degree of polymerization of the redox polymers, and the electrode is active only in strong acidic solutions because electron mediators are coupled with polymers only in a strong acidic solution.

It has also been well known that an electron mediator such as methyl viologen is used in the form of a solution or a suspension with an unmodified electrode or with a chemically modified electrode. In this case, a large amount of an electron mediator has to be used and, in some cases, an electrochemically inactive material which may decrease the current efficiency has to be added to the solution.

The object of this invention is to provide a new type of chemically modified electrode, on which various kinds of electron mediators can be easily immobilized, with a wide variety of applications, whereby the above-mentioned disadvantages have been solved. The concept of this invention is the preparation of an electrode which comprises an electrically conducting solid electrode on which a strong acidic cation exchange resin containing aromatic groups and a nitrogen-containing electron mediator are immobilized.

This invention is based on the present inventors' finding that nitrogen-containing electron mediators are immobilized with a strong acidic cation exchange resin containing aromatic groups on electrically conducting solid electrodes and these electrodes can be used as stable chemically modified electrodes.

The electrically conducting solid electrodes according to this invention are, for example, (a)metal electrodes such as platinum and nickel, (b)carbonaceous electrodes such as glassy carbon and pyrolytic graphite, and (c)metal oxide semiconductor electrodes such as tin oxide and titanium oxide.

A typical example of a strong acidic cation exchange resins of this invention is polystyrenesulfonate(PSS).

Examples of nitrogen-containing electron mediators are viologens, cytochrome $c_3$, NAD(nicotinamide-adenine dinucleotide), ferredoxins, methyl-substituted phenylenediamines, and metal complexes composed of a metal such as ruthenium, iron or osmium and a ligand such as 2,2'-bipyridine or 1,10-phenanthroline. Among those nitrogen-containing electron mediators, methyl viologen(1,1'-dimethyl-4,4'-bipyridinium salts, i.e., MV, such as its dichloride) is preferable.

Another role of PSS is to stabilize some unstable electron mediators such as phenazine and its derivatives. In other words, some unstable electron mediators such as phenazine and its derivatiaves are stabilized by forming a complex with PSS.

In the polymer coated electrode of the present invention, the nitrogen-containing electron mediator is immobilized up to the maximum ion exchange capacity of the said cation exchanger. For example, in the case of MV, four sulfonate groups in PSS immobilize one MV molecule. When an excess amount of MV is added to the said polymer, MV dissolves out from the electrode into the solution. The saturation of the electron mediator in the polymer is unnecessary. The polymer which contains the electron mediator down to one tenth of the saturation is still applicable for practical purposes.

The polymer coated electrode according to the present invention has the following advantages over the previously reported polymer coated electrodes, namely, (1) The pH of the solution used as a reaction medium can be in the range between 4 and 10. That is, strongly acidic media, which have been used for the previously reported polymer coated electrode and are unfavorable to most of reactions, are unnecessary.

(2) Electron mediators are monomeric, and easily and quantitatively immobilized in PSS. The synthesis of the polymeric mediators as previously reported for the purpose of immobilization is tedious and difficult.

(3) Unstable electron mediators such as phenazine and its derivatives become stable when these electron mediators are coupled with PSS.

(4) The polymer coated electrodes containing an electron mediator are stable and the thickness of the film is only a few microns. That is, only a small amount of electron mediator is necessary to build the electrode.

(5) The polymers coated on the electrodes are moderately hydrophilic and the electron mediators in the polymer do not dissolve out into the reaction medium.

Therefore, the polymer coated electrode according to the present invention can be used as it is or can be used in combination with various chemical species and/or light energy.

The second object of this invention is to provide a hydrogen electrode comprising a polymer coated electrode on which a strongly acidic cation exchange resin and a nitrogen-containing electron mediator are immobilized, and a redox system which is coupled to said electron mediator on the electrode.

Examples of the redox systems employed are hydrogenases, nitrogenases, bacteria, ferredoxins, cytochromes and NADH.

One of the redox systems is either dissolved or suspended in the reaction medium such as phosphate buffer or tris-HCl buffer at pH 7.0, and the polymer coated electrode of the present invention is immersed into it as an anode. The counter electrode acting as a cathode may be a conventional electrode such as platinum or carbon electrode, or a polymer coated electrode of the present invention and so on. In the solution of hydrogenase, hydrogen is quantitatiavely generated by electrolysis in the cathodic compartment, and oxygen is generated at the counter electrode in the pH range between 4 and 10. When the said redox system is immobilized on the polymer coated electrode of the present invention, the efficiency of electrolysis is improved remarkably and the consumption of the said redox system can be lowered.

The third object of this invention is to provide an oxygen electrode by immobilizing redox systems such as chloroplasts and living green algae together with a strong acidic cation exchange resin containing aromatic groups and a nitrogen-containing electron mediator such as viologens on an electrically conducting solid electrode. This oxygen electrode is immersed into the above mentioned buffer solutions. When the polymer coated electrode with living green algae or chloroplasts is illuminated, an electron is eliminated from water by living green algae or chloroplasts and oxygen is generated. Simultaneously, hydrogen is generated at the counter electrode. Thus, an electric current is obtained.

Bacterial chloroplasts are much more favorable than plant chloroplasts because oxygen, which depresses the current intensity, is not generated at the photo-anode.

The fourth object of this invention is to provide a voltametric detector of biologically active substances by using polymer coated electrodes of the present invention.

The polymer coated electrodes of the present invention show a linear current-concentration relationship to a biologically active substance when an appropriate electron mediator is chosen. Thus, this electrode is applicable to biological substances as a voltammetric detector.

After a biological substance separated by a suitable method such as chromatography is added into an electrolytic solution at pH 4–10, the solution is electrolyzed in a flow cell with the polymer coated electrode of the present invention and an appropriate counter electrode. The electrolytic current is proportional to the concentration of the biologically active substances. Thus the concentration of the biologically active substance can be quantitatively determined by the measurement of the current.

Examples of favorable combinations of the nitrogen-containing electron mediator with biologically active substances are:

(i) MV with cytochrome c, hemoglobin, mioglobin, NAD, hydrogenase and E. coli, (ii) ferredoxins with hydrogenase, nitrogenase, cytochrome c, NAD and NADP(NAD phosphate), (iii) cytochrome $c_3$ with hydrogenases isolated from sulfate reducing bacteria, and (iv) NAD with glucose.

The fifth object of this invention is to provide a photochromic display by using a polymer coated electrode of the present invention such as MV-PSS polymer coated $SnO_2$ electrode(NESA glass). When chloroplast is also immobilized on the electrode as described above, the efficiency as photochromic display is improved. When these electrodes are illuminated, the polymer film is colored while it becomes colorless in the dark. The photochromic behavior of the polymer coated electrodes is similar to that of the prior-art polymerized viologen coated electrode.

The preparation of the polymer coated electrode of the present invention is as follows;

A strongly acidic cation-exchange resin with aromatic groups is immobilized on an electrical conducting solid by (i) plasmapolymerization, (ii) mixing with polyvinyl alcohol, or (iii) mixing with collodion solution. A nitrogen-containing electron mediator is spread on the surface of an electrical conducting solid with the said cation exchange resin and polyvinyl alcohol, collodion or acetylcellulose solution. Bovine serum albumin is added to the polyvinyl alcohol solution as a bridging agent with which the stability of the polymer film on the electrical conducting solid is remarkably improved.

The immobilization of chloroplasts and living green algae on the above-mentioned polymer coated electrode can be made by spreading chloroplasts(or green algae) in PVA solution or in collodion solution on the PSS film. Bovine serum albumin also stabilizes chloroplasts(or green algae) on the polymer film. These electrodes are used as photoanodes to generate oxygen.

A hydrogenase-coated hydrogen electrode of this invention may be prepared acording to a conventional method, e.g., by immobilizing hydrogenases with polyacylamide gel on the above mentioned polymer coated electrode.

The invention is further illustrated with reference to the following examples and comparative experiments, but not intended to be restricted by them.

EXAMPLE I

Preparation of tin oxide-coated glass electrode

Tin oxide film with about 50 nm thickness is deposited on an optically polished glass plate so that an optically transparent electrode(OTE) with a resistivity of 20 ohms/square is prepared. A rectangular $SnO_2$ coated glass plate ($10 \times 15$ mm) is rinsed with acetone and then by distilled water. A copper wire is connected to the $SnO_2$ film by a silver epoxy composite resin and then insulated by an epoxy resin. After the surface of the electrode is successively rinsed by methanol, acetone and then distilled water, the $SnO_2$ surface is soaked in a concentrated sulfuric acid for 5–30 seconds. Then, the surface is rinsed again by distilled water, methanol, acetone, and, finally, by distilled water.

EXAMPLE II

Preparation of an MV-PSS film coated electrode (1) Chemicals used (i) PSS

Sodium polystyrenesulfonate (NaPSS) ($\overline{Mw}=7,500$; degree of sulfonation$=73.4\%$); ammonium polystyreneslfonate($NH_4PSS$) ($\overline{Mw}=25,000$; degree of sulfonation$=51.6\%$); polystyrenesulfonic acid ($\overline{Mw}=1,000,000$; degree of sulfonation$=51.0\%$)

(ii) MV(manufactured by BDH and by Wako Chemical Co.)

(iii) Polyvinyl alcohol(manufactured by Kurare Co., Kurare-117 (degree of polymerization$=1,700$)

(iv) Bovine serum albumin(Sigma Chemical Co.)

(2) Preparation of MV-NaPSS-PVA solution 3 g of polyvinyl alcohol (PVA) is dissolved into 20 ml of distilled water at room temperature. Then 0.2 g of MV and 0.7 g of NaPSS is dissolved into the above solution by heating it gradually up to the boiling temperature, and then the mixture is cooled down to room temperature. If it is desired to use a bridging agent, about 1% by weight of bovine serum albumin per gram of PVA is added to the above mixture.

(3) Immobilization of the polymer film on tin oxide coated glass

The above mentioned MV-NaPSS-PVA solution is spread on an NESA glass(tin oxide-coated glass electrode) uniformly so that thin polymer film is obtained. This polymer coated NESA glass is dried over silica gel in the dark for more than one day. Then, it is dried in an oven for 15 mins. at 190° C. The dry weight of the polymer film is 1.5 mg.

EXAMPLE III

Preparation of a chloroplast-MV-PSS film coated electrode (1) Preparation of chloroplast-PVA mixture 3 g of PVA is dispersed into 20 ml of distilled water at room temperature, and then this mixture is heated gradually up to the temperature just below the boiling point. After an uniform solution is obtained, it is cooled gradually to room temperature. When a bridging agent is desired, about 1% by weight of bovine serum albumin per gram of PVA is added to this polymer solution. Then, 0.28 g *Anabaena cylindrica* suspension (which contains about 3% by weight of chlorophyll) is suspended into this polymer solution.

(2) Immobilization of chloroplasts(green algae) on the polymer coated electrode

Chloroplasts(green algae-suspended in PVA solution described under 1) above is spread uniformly on the polymer coated electrode described in Example II-3), and then it is dried over a desiccant at 0°-5° C. in the dark. The weight of the film is 2 mg.

A mixture of 0.4 g of chloroplasts(green algae)-PVA solution described under 1 above and 0.4 g of MV-NaPSS-PVA solution described in Example II-2) can also be used. This mixture is spread on an NESA glass plate so that a composite polymer coated electrode is obtained.

Protoplasm of different kinds of green algae such as *Bryopsis maxima* and *Bryopsis plumosa* and photosynthetic bacteria such as *Chromatium vinosum* and their chromatophore from the photosynthetic bacteria have the same functions as *Anabaena cylindrica* to photo-responses.

EXAMPLE IV

Preparation of a chloroplast-MV-PSS film coated electrode (1) Preparation of chloroplast-collodion solution 0.03 g of *Anabaena cylindrica* suspension as described in Example III is mixed with 0.9 g of collodion solution, and the mixture is kept for 10 minutes at room temperature. The mixture is separated into three layers.

(2) Immobilization of chloroplasts(green algae) on the polymer coated electrode

The top two layers of the chloroplast-collodion solution described under 1 above is spread on the polymer coated electrode described in Example II-3 and then it is dried over a desiccant in the dark. The weight of the film is 1.5 mg.

Different kinds of green algae and chloroplasts can be used in the same way as *Anabaena cylindrica* as in Example III.

EXAMPLE V

MV-NaPSS polymer film coated electrode

A mixture of 0.88 mg of NaPSS(about 0.5 m mole) and 0.095 g of MV(about 50 m mole) is dissolved into 10 ml of distilled water. 0.5 ml of acetylcellulose-saturated acetone solution is added to 0.5 ml of the above-mentioned solution, and a white precipitate is formed. An excess amount of acetone is added to this suspension.

The drop of this suspension taken by a microsyringe is dispersed on a pyrolytic graphite electrode (0.5 cm diameter, 0.2 $cm^2$) and then dried in the dark so that polymer coated graphite is prepared.

EXAMPLE VI

Oxygen electrode

*Anabaena cylindrica* is used as one of photo-systems.

Three different photoanodes are prepared, i.e., i) An NESA glass electrode on which *Anabaena cylindrica* (green algae) is immobilized, (ii) MV-PSS polymer film coated electrode described in Example II-3 and (iii) MV-PSS polymer coated electrode on which *Anabaena cylindrica* is immobilized as is described in Example IV-2.

These photo-anodes are coupled with a platinum cathode in a phosphate buffer solution at pH 7. These photo-anodes are illuminated by a Xe-lamp and photo-currents are measured with a zero-resistance ammeter.

The following table illustrated the photo-current of various photo-anodes. The photo-currents are given by the difference between the current under the illumination and that in the dark.

TABLE 1

| Electrode | $SnO_2$ | $SnO_2$—chloroplast | $SnO_2$—chloroplast | $SnO_2$—PSS—MV | $SnO_2$—PSS—MV-chloroplast |
|---|---|---|---|---|---|
| Drying Conditions | | room temp. | 0-5° C. | 190° C. | 0-5° C. |
| photo-current* | 0.12 | 0.21 | 0.41 | 0.53 | 2.31 |

*arbitrary unit

It is obvious from this table that the MV-PSS polymer film on the electrode improves the optical yield of the photo-electric current remarkably. The MV-PSS polymer film on the electrode employed in the present invention is very stable and the loss of MV from the polymer film is within 5% after 100-1000 repetitions of the experiment.

EXAMPLE VII

Electrochemical sensor for biologically active substances

An MV-PSS polymer film is immobilized on an NESA glass ($3 \times 10^{-2} cm^2$) and is employed as an electrochemical detector of biologically active substances. The current is proportional to the concentration of the biologically active substances.

In the case of cytochrome c, the current is 1.25 micro amperes for a concentration of 0.1 m M and the plots of the current against the concentration passes through the origin. In the case of hemoglobin, the current is 5 micro amperes for a concentration of 0.1 m M.

EXAMPLE VIII

Photochromic display

The polymer coated electrode described in Example II-3 becomes deep blue under the sun light and becomes colorless in the dark. The polymer coated electrode, on which chloroplasts(green algae) are immobilized, described in Example IV-2 shows the same behavior as the above-mentioned electrode.

What is claimed is:

1. An electrically conducting solid electrode having a surface on which a monomeric nitrogen-containing electron mediator and a strong acidic cation exchange resin containing sulfonated, aromatic groups are immobilized.

2. The electrically conducting solid electrode as set forth in claim 1, where said strong acidic cation exchange resin is polystyrenesulfonic acid.

3. The electrically conducting solid electrode as set forth in claim 1, where said electron mediator is a viologen, cytochrome $C_3$, nicotinamide-adenine dinucleotide (NAD), a ferredoxin, or a methyl-substituted phenylenediamine or a metal complex composed of a metal selected from the group consisting of ruthenium, iron and osmium and a ligand selected from the group consisting of 2,2'-bipyridine and 1,10-phenanathroline.

4. The electrically conducting solid electrode as said forth in claim 1, wherein said resin is immobilized on said surface by plasma-polymerization or by coating said surface with a mixture of said resin and either poly-vinyl alcohol or collodin solution and in a second step said mediator is coated on said surface in combination with said resin and either poly-vinyl alcohol, collodin, or acetylcellulose.

5. The electrically conducting solid electrode as set forth in claim 1, wherein the nitrogen-containing electron mediator is present in an amount less than the capacity of the cation exchange resin.

6. The electrically conducting solid electrode as set forth in claim 5, wherein the nitrogen-containing electron mediator is present in an amount at least one tenth of the capacity of the cation exchange resin.

7. A hydrogen electrode which comprises (a) an electrically conducting solid electrode on the surface of which a monomeric nitrogen-containing electron mediator and a strong acidic cation exchange resin containing aromatic groups are immobilized and (b) a redox system which is coupled to said electron mediator on the electrode, where the redox system is hydrogenase, nitrogenase, bacterium, ferrodoxin or NADH.

8. An oxygen electrode, which comprises an electrically conducting solid electrode on the surface of which a strong acidic cation exchange resin containing aromatic groups, a monomeric viologen and a chloroplast are immobilized.

9. A voltammetric detector of biologically active substances comprising an electrically conducting solid electrode on which a strong acidic cation exchange resin containing aromatic groups, a monomeric nitrogen-containing electron mediator and a biologically active substance are immobilized.

10. A photochromic display element, comprising an electrically conducting solid electrode on the surface of which a composition comprising (a) a strong acidic cation exchange resin containing aromatic groups and (b) a monomeric nitrogen-containing electron mediator and (c) a chloroplast are immobilized.

* * * * *